US006804360B1

(12) United States Patent
Misawa et al.

(10) Patent No.: US 6,804,360 B1
(45) Date of Patent: Oct. 12, 2004

(54) AIR INTAKE NOISE REDUCTION APPARATUS FOR AUTOMOTIVE VEHICLE

(75) Inventors: Kichiji Misawa, Saitama (JP); Minoru Hasegawa, Hyogo (JP)

(73) Assignees: Honda Giken Kogyo Kabushiki Kaisha, Tokyo (JP); Tigers Polymer Corporation, Toyonaka (JP)

( * ) Notice: Subject to any disclaimer, the term of this patent is extended or adjusted under 35 U.S.C. 154(b) by 0 days.

(21) Appl. No.: 09/419,785

(22) Filed: Oct. 18, 1999

(30) Foreign Application Priority Data

Oct. 19, 1998 (JP) ....................................... P. 10-297113

(51) Int. Cl.[7] ............................ A61F 2/20; H04B 27/00

(52) U.S. Cl. .................... 381/71.5; 381/71.4; 381/71.1; 381/86

(58) Field of Search .............................. 381/71.1, 71.4, 381/71.5, 86

(56) References Cited

U.S. PATENT DOCUMENTS

| | | | | |
|---|---|---|---|---|
| 2,926,745 A | | 3/1960 | Leistritz | 181/268 |
| 5,778,081 A | * | 7/1998 | Patrick | 381/71.5 |
| 5,828,759 A | * | 10/1998 | Everingham | 381/71.5 |
| 6,084,971 A | * | 7/2000 | McLean | 381/71.5 |
| 6,088,458 A | * | 7/2000 | Hasegawa et al. | 381/71.4 |

FOREIGN PATENT DOCUMENTS

| | | |
|---|---|---|
| DE | D. 599 295 | 7/1934 |
| DE | 295 06 424 | 7/1995 |
| EP | 0 541 016 | 5/1998 |
| FI | 981 074 A | 5/1998 |
| GB | 275 437 | 8/1927 |
| WO | WO 99/58824 | 11/1999 |

OTHER PUBLICATIONS

Patent Abstracts of Japan, vol. 1996, No. 10, Oct. 31, 1996, and JP 8–158965 A (Honda Motor Co., Ltd.), Jun. 18, 1996 * abstract *.

* cited by examiner

*Primary Examiner*—Minsun Oh Harvey
*Assistant Examiner*—Laura A. Grier
(74) *Attorney, Agent, or Firm*—Armstrong, Kratz, Quintos, Hanson & Brooks, LLP

(57) ABSTRACT

An air intake noise reduction apparatus is provided which can effectively reduce air intake noise even with simple construction requiring a small number of components. Four air intake passages 24, 25, 26, 27 which each have different passage lengths are formed by connecting an upper wall 17 and a lower wall 18 of an air intake noise reduction duct 11 which are flattened in a vertical direction with three partition walls 21, 22, 23. Air intake noise can be reduced by making pulsating air interfere with one another which is generated in the plurality of air intake passages 24, 25, 26, 27 which each have the different passage lengths in such a manner as to have different phases shifted from one another. In addition, since the partition walls function as a reinforcement rib, the rigidity of the air intake noise reduction duct 11 can be enhanced. Moreover, since the partition walls are formed in such a manner as to extend along an intake air flow direction, increase in intake air resistance can be suppressed to a minimum level.

13 Claims, 8 Drawing Sheets

AIR INTAKE NOISE REDUCTION APPARATUS FOR AUTOMOTIVE VEHICLE

BACKGROUND OF THE INVENTION

1. Field of the Invention

The present invention relates to an air intake noise reduction apparatus for an automotive vehicle for reducing air intake noise using an air intake noise reduction duct for inducting air into an engine.

2. Description of Related Art

A single-stage interference-type air intake noise reduction apparatus and a multi-stage resonance-type air intake noise reduction apparatus are known as an air intake noise reduction apparatus for reducing air intake noise originating from an internal combustion engine of an automotive vehicle. As shown in FIG. 10A, the single-stage interference-type air intake noise reduction apparatus is constructed so as to exhibit an air intake noise reduction effect through interference between pulsating air in an air intake passage 01 and pulsating air in a by-pass passage 02 formed as part of the air intake passage 01 whose phases are shifted due to the difference in length L1, L2 of the air intake passage 01 and the by-pass passage 02. In addition, as shown in FIG. 10B, the multi-stage resonance-type air intake noise reduction apparatus is constructed so as to exhibit an air intake noise reduction effect through resonance of air in a plurality of integrally formed resonance chambers 03, 04 which are made to communicate with an air intake passage 05.

Moreover, Japanese Patent Unexamined Publication (Kokai) No. Hei.8-158965 describes an air intake noise reduction apparatus in which an expansion-type air intake noise reduction apparatus and a resonance-type air intake noise reduction apparatus are integrally provided in a common air intake noise reduction case.

With the single-stage interference-type air intake noise reduction apparatus shown in FIG. 10A, since it is single-staged, not only does the frequency range become narrow where the air intake noise reduction effect is exhibited, but also there needs to form the by-pass passage separately from the air intake passage, these resulting in disadvantages in cost and space. If this single-stage construction is transformed into a multi-stage construction, the air intake noise reduction effect can be exhibited within a wider frequency range, but it gets more disadvantageous in terms of cost and space.

With the multi-stage resonance-type air intake noise apparatus shown in FIG. 10B, since it needs wider space, not only does the size of the apparatus have to get larger, but also the construction of the apparatus gets complicated, which makes it difficult to mold components required for such a complicated construction, thus leading to a problem of increase in cost.

Furthermore, Japanese Patent Unexamined Publication No. HEI 8-158965 also describes an air intake noise reduction apparatus which is so complicated in construction that molding of components required for such a complicated construction becomes difficult, thus posing a problem of increase in cost, as well as a problem of increase in manhour for assembly of a large number of components attributed to the complicated construction.

SUMMARY OF THE INVENTION

The present invention was made in view of the aforesaid circumstances, and it is an object of the present invention to provide an air intake noise reduction apparatus for effectively reducing air intake noise, although it is simple in construction and therefore requires a small number of components.

With a view to attaining the aforesaid object, according to a first aspect of the present invention, there is provided an air intake noise reduction duct for an automotive vehicle for reducing air intake noise with an air intake noise reduction duct for inducting air into an engine of the automotive vehicle, wherein a plurality of air intake passages which each have different passage lengths are formed by partitioning the air intake noise reduction duct with partition walls.

In the present invention, the object can be achieved by an air intake noise reduction apparatus for an automotive vehicle for reducing air intake noise with an air intake noise reduction duct for inducting air into an engine of the automotive vehicle, wherein a plurality of air intake passages which each have different passage lengths are formed by partitioning the air intake noise reduction duct with partition walls.

According to the above construction, although the apparatus is constructed as a compact and low-cost construction comprising only the partition walls provided in the air intake noise reduction duct, air intake noise can effectively be reduced by forming the plurality of air intake passages which each have different passage lengths, and in addition, the rigidity of the air intake noise reduction duct can be increased with the partition walls functioning as a reinforcement rib.

In the above-mentioned construction, it is advantageous that the partition walls extend along an intake air flow direction.

Since the partition walls are formed in such a manner as to extend along the air intake direction, the increase in intake air resistance can be suppressed to a minimum level.

In addition, according to a second aspect of the invention, there is provided an air intake noise reduction apparatus for an automotive vehicle for reducing air intake noise with an air intake noise reduction duct for inducting air into an engine of the automotive vehicle, wherein a plurality of air intake passages which each have different passage lengths are formed by connecting together opposed walls which each have the largest surface area of a flat portion provided as part of the air intake noise reduction duct with partition walls extending along an air intake direction.

According to the above construction, although the apparatus is constructed with a compact and low-cost construction comprising only the partition walls provided in the air intake noise reduction duct, air intake noise can effectively be reduced by forming the plurality of air intake passages which each have different passage lengths, and in addition, since the partition walls connecting together the opposed walls each having the largest surface area of the flat portion function as a reinforcement rib, the rigidity of the air intake noise reduction duct can be increased to thereby effectively prevent membrane surface vibrations. Moreover, since the air intake noise reduction duct has the flat portion, the apparatus can be disposed even in a narrow space in an engine compartment.

Furthermore, according to a third aspect of the invention, there is provided an air intake noise reduction apparatus for an automotive vehicle for reducing air intake noise with an air intake noise reduction duct for inducting air into an engine of the automotive vehicle, wherein a plurality of air intake passages which each have different passage lengths are formed by partitioning a curved portion provided in the air intake noise reduction duct with partition walls extending in such a manner as to conform to a curved configuration of the curved portion.

According to the above construction, although the apparatus is constructed as a compact and low-cost construction comprising only the partition walls provided in the air intake noise reduction duct, air intake noise can effectively be reduced by forming the plurality of air intake passages which each have different passage lengths, and in addition, the rigidity of the air intake noise reduction duct can be increased with the partition walls functioning as a reinforcement rib. Moreover, since the curved portion of the air intake noise reduction duct is partitioned with the partition walls extending in such a manner as to conform to the curved configuration of the curved portion, not only can the air intake noise reduction duct be made compact further in size, but also the increase in intake air resistance can be suppressed by straightening the flow of air at the curved portion.

In addition, according to a fourth aspect of the invention, there is provided an air intake noise reduction apparatus for an automotive vehicle as set forth in the third aspect of the present invention, wherein the length of the partition walls is made shorter as the partition walls are situated more radially inwardly of the curved portion.

According to the above construction, since at least three air intake passages are formed with at least two partition walls, the air intake noise reduction effect can be enhanced. In addition thereto, since the length of the partition wall situated more radially inwardly in the curved portion becomes shorter, the air intake noise reduction duct can further be made compact in size.

Moreover, according to a fifth aspect of the invention, there is provided an air intake noise reduction apparatus for an automotive vehicle for reducing air intake noise with an air intake noise reduction duct for inducting air into an engine of the automotive vehicle, wherein a plurality of air intake passages which each have different passage lengths are formed by partitioning an air intake noise reduction duct with partitioning walls, and wherein the direction of intake air flow and the direction of the partition walls are made to intersect each other at an entry portion of the air intake noise reduction duct.

According to the above construction, although the apparatus is constructed as a compact and low-cost construction comprising only the partition walls provided in the air intake noise reduction duct, air intake noise can effectively be reduced by forming the plurality of air intake passages which each have different passage lengths, and in addition, the rigidity of the air intake noise reduction duct can be increased with the partition walls functioning as a reinforcement rib. Moreover, since the direction of intake air flow and the direction of the partition walls are made to intersect each other at an entry portion of the air intake noise reduction duct, penetration of water or the like into the interior of the air intake noise reduction duct can be checked.

The present disclosure relates to subject matter contained in Japanese Patent Application No. Hei. 10-297113, filed on Oct. 19, 1998, and which is expressly incorporated herein by reference in its entirety.

DETAILED DESCRIPTION OF THE PREFERRED EMBODIMENTS

A preferable embodiments of the present invention will be described below in the accompanying drawings.

Figure 1:
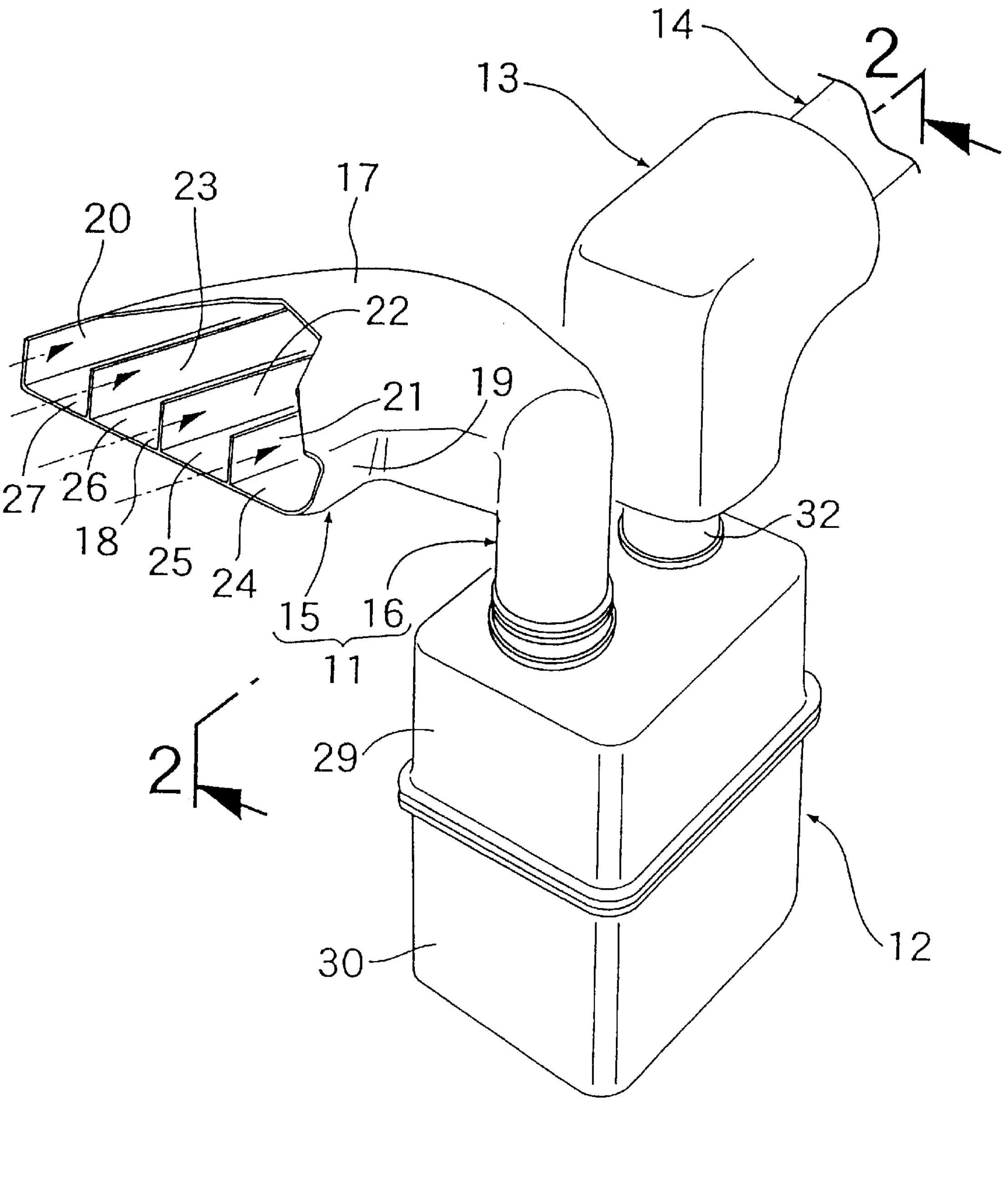
FIG. 1 is an overall perspective view of an air intake noise reduction duct.
Figure 2:
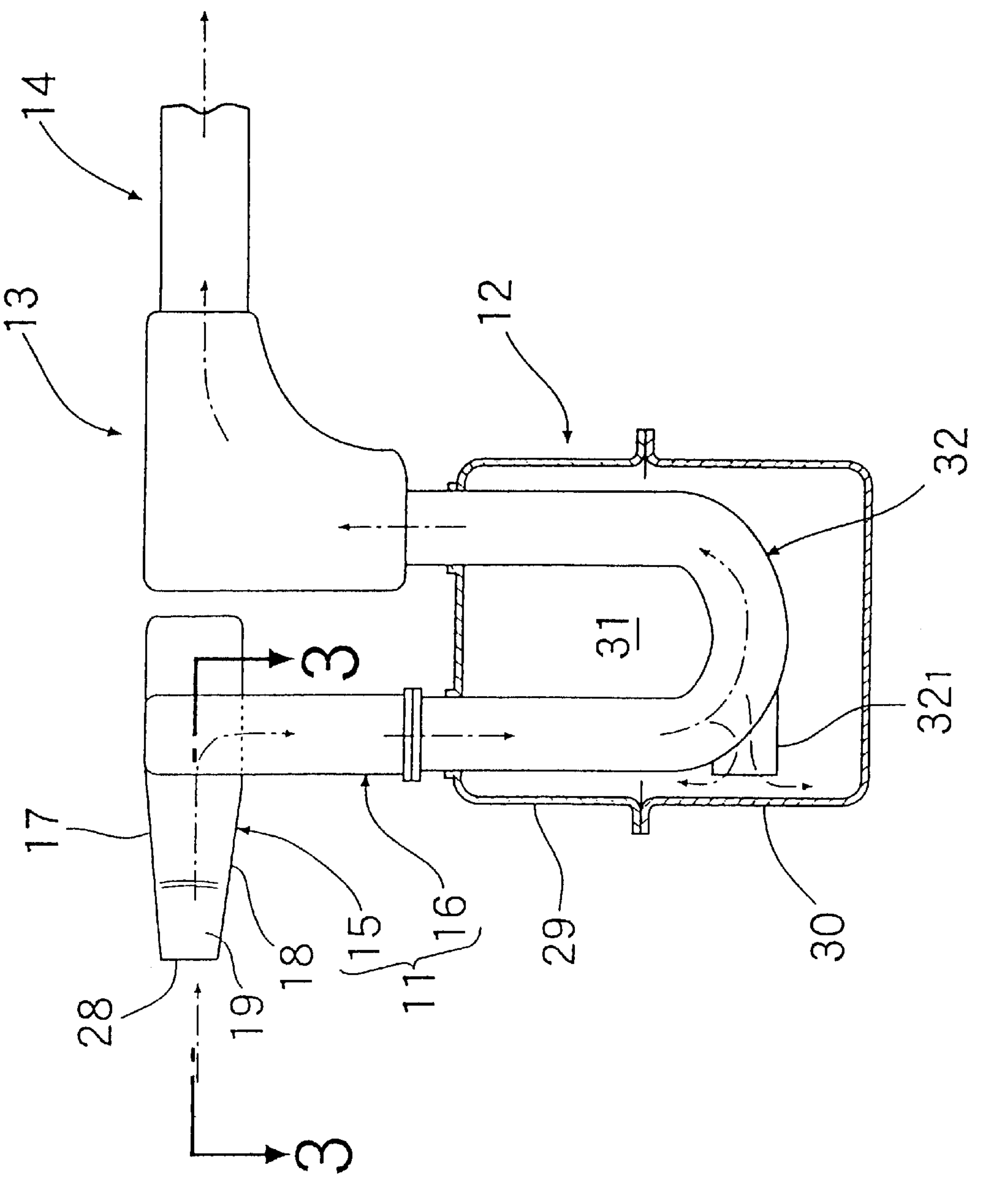
FIG. 2 is a sectional view taken along the line 2—2 of FIG. 1.
Figure 3:
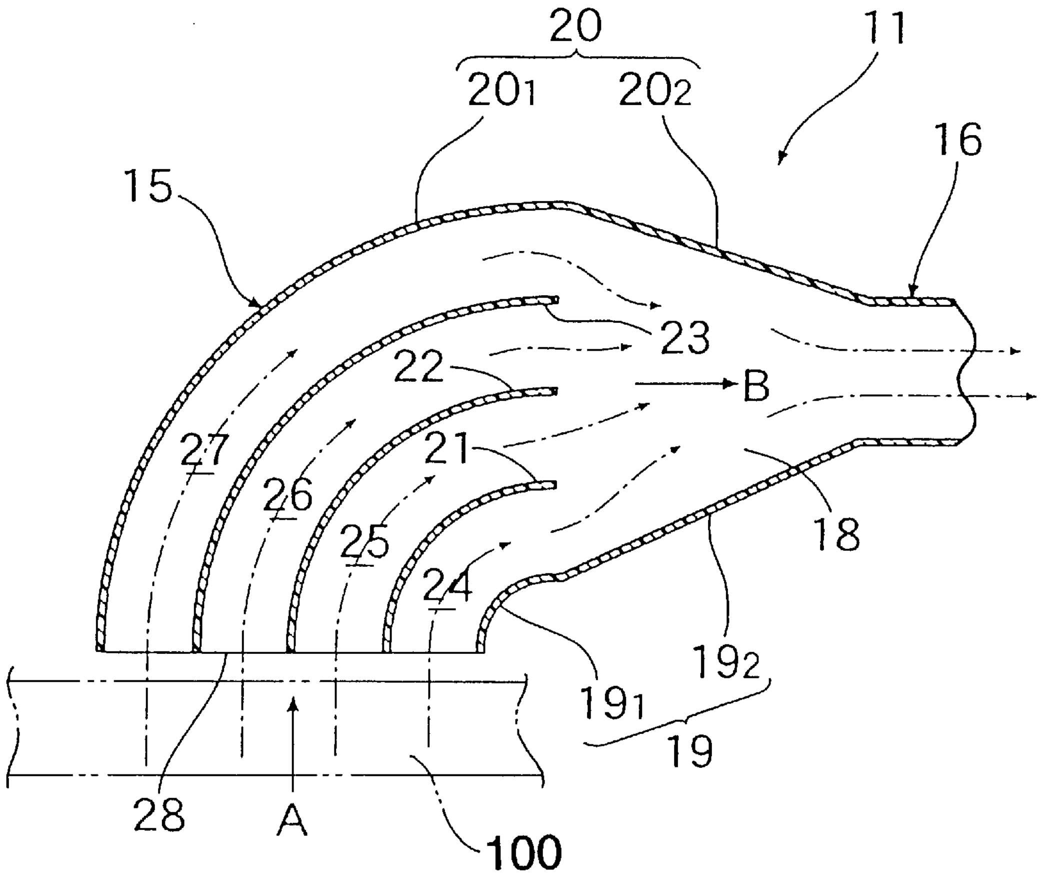
FIG. 3 is a sectional view taken along the line 3—3 of FIG. 2.
Figure 4:
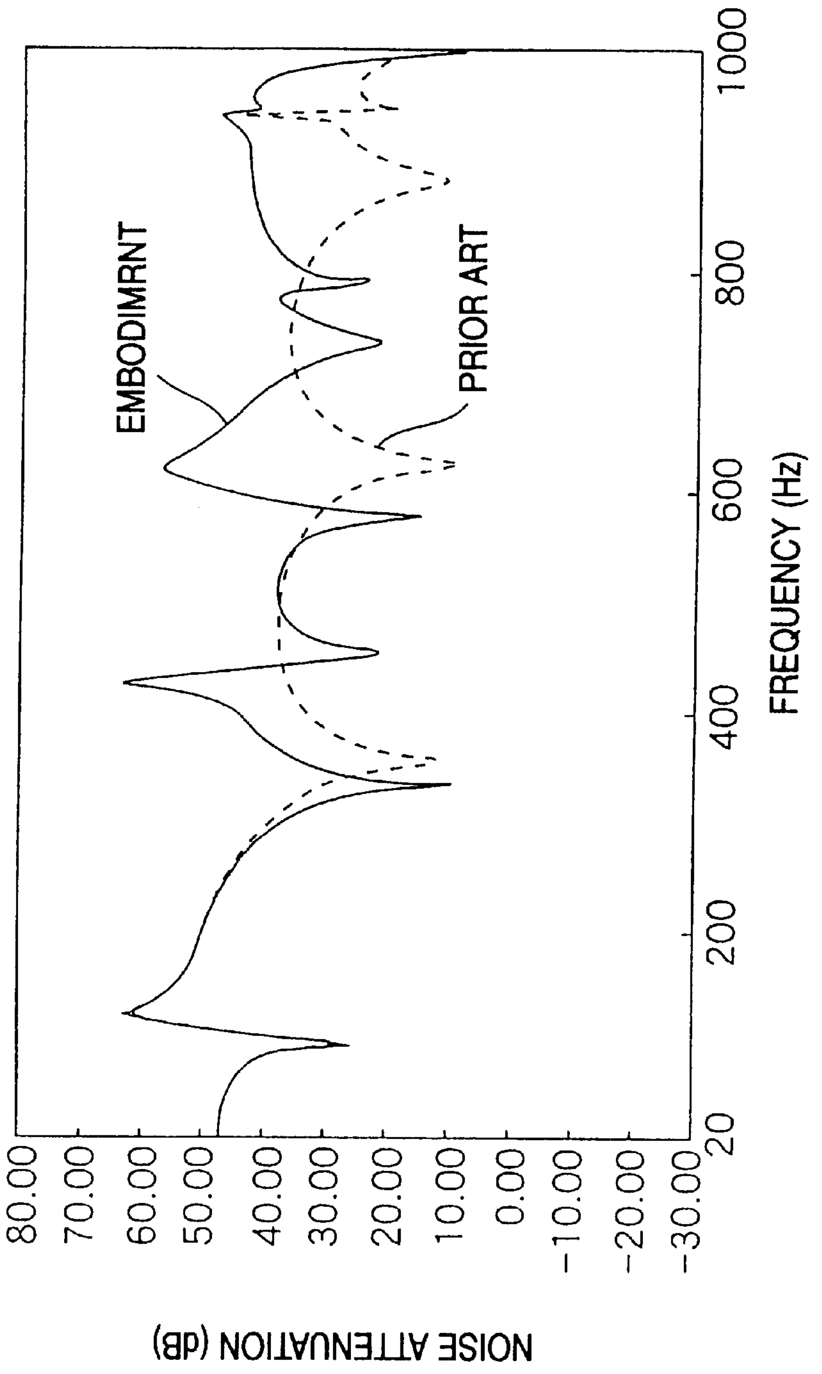
FIG. 4 is a graph explaining an effect provided by the air intake noise reduction duct.

FIGS. 1 to 4 show a first embodiment of the present invention, wherein FIG. 1 is an overall perspective view of an air intake noise reduction apparatus, FIG. 2 is a sectional view taken along the line 2—2 of FIG. 1, FIG. 3 is a sectional view taken along the line 3—3 of FIG. 2, and FIG. 4 is a graph explaining an effect provided by the air intake noise reduction apparatus.

As shown in FIGS. 1 to 3, provided from an upstream side to a downstream side along an air intake system of an engine of an automotive vehicle are an air intake noise reduction duct 11, a resonator 12, an air cleaner 13 and an air flow tube 14. Air taken in from the air intake noise reduction duct 11 is fed into an engine, not shown, via the resonator 12, the air cleaner 13, the air flow tube 14 and a throttle body, not shown.

The air intake noise reduction duct 11 is constituted by a single member which is blow molded of a synthetic resin and comprises a duct distal end portion 15 having a configuration flattened in a vertical direction and a duct proximal end portion 16 having a circular cross-section which is continuous with the duct distal end portion 15 and extending downward. The duct distal end portion 15 comprises a flat upper wall 17 and a flat lower wall 18 which are disposed in parallel with each other, and these upper wall 17 and lower wall 18 are connected to each other by a pair of side walls 19, 20 so as to form a closed cross-section flattened in the vertical direction. In addition, these upper wall 17 and lower wall 18 constitute opposed walls each having the largest surface area of the air intake noise reduction duct 11.

As is clear from FIG. 3, the side walls 19, 20 each comprise an arc portion$\mathbf{19_1}$, $\mathbf{20_1}$ and a tapered portion $\mathbf{19_2}$, $\mathbf{20_2}$, the arc portions $\mathbf{19_1}$, $\mathbf{20_1}$ sharing the same curvature center and the tapered portions $\mathbf{19_2}$, $\mathbf{20_2}$ being not in parallel with each other. The arc portion $\mathbf{19_1}$ of the side wall 19 is formed short and radially inwardly, while the arc portion $\mathbf{20_1}$ of the other side wall 20 is formed long and radially outwardly. In addition, the tapered portions $\mathbf{19_2}$, $\mathbf{20_2}$ of the side walls 19, 20 approach each other as they extend toward a downstream side of the air intake noise reduction duct and the duct proximal end portion 16 having a circular cross section is connected smoothly thereto. Moreover, the upper wall 17 and the lower wall 18 are connected by three partition walls 21, 22, 23 sharing the same curvature center as that of the arc portions $\mathbf{19_1}$, $\mathbf{20_1}$ and having different lengths, and four arc-like air intake passages 24, 25, 26, 27 are constituted by the arc portions $\mathbf{19_1}$, $\mathbf{20_1}$ and the partition walls 21, 22, 23. The three partition walls 21, 22, 23 connecting the upper wall 17 and the lower wall 18 each having the largest surface area of the air intake noise reduction duct 11 are disposed in such a manner as to extend along the air intake direction.

The passage lengths of the four air intake passages are all different, and the length of the air intake passage is designed to become longer sequentially from the air intake passage 24 which is the shortest of the four and situated innermost in a curved direction, in other words, in a radial direction to the air intake passage 27 which is the longest and situated outermost in the radial direction. Since the air intake passages 24, 25, 26 27 are curved, a direction A in which air flows into opening ends 28 of the air intake passages 24, 25, 26, 27 and a direction B in which air flows out from the air intake passages 24, 25, 26, 27 is shifted 90 degrees from each other.

The resonator 12 is divided vertically into two halves; an upper housing 29 and a lower housing 30, and an intake air resonance chamber 31 is formed in the resonator 12. An air intake duct 32 formed substantially into a U-shape and received in the interior of the intake air resonance chamber 31 penetrates through an upper wall of the upper housing 29 to thereby be connected to a downstream end of the air intake noise reduction duct 11 at an upper stream end thereof, while it penetrates through the upper wall of the housing 29 to thereby be connected to the air cleaner 13 at a downstream end thereof. An intermediate portion of the air intake duct 32 is adapted to communicate with the internal space of the intake air resonance chamber 31 via a communicating tube $\mathbf{32}_1$.

Next, an operation of the embodiment of the present invention constructed as described above will be described below.

Air taken in from the air intake noise reduction duct 11 by virtue of intake negative pressure produced when an engine of an automotive vehicle is in operation is supplied into the engine via the resonator 12, the air cleaner 13, the air flow tube 14 and the throttle body. When this happens, since the interior of the air intake noise reduction duct 11 is partitioned with the three partition walls 21, 22, 23 so as to form the four air intake passages 24, 25, 26, 27 which each have different passage lengths, pulsating air generated in the respective air intake passages 24, 25, 26, 27 by the engine acting as a sound source and having different phases interfere with one another and air intake noise is reduced over a wide frequency region. In addition, in the resonator 12 connected to the downstream side of the air intake noise reduction duct 11, since the communicating pipe $\mathbf{32}_1$ of the air intake duct 32 received in the interior of the resonator 12 is caused to communicate with the intake air resonance chamber 31, air intake noise in a relatively low frequency region is reduced by virtue of a resonance effect provided by the intake air resonance chamber 31 having a large capacity.

FIG. 4 is a graph showing noise attenuation effected at each frequency region and it is seen from the graph that the air intake noise reduction effect is obtained over a wide frequency range by the air intake noise reduction apparatus according to the present invention.

Moreover, since the air intake noise reduction apparatus is constructed with a simple construction in which the upper wall 17 and the lower wall 18 of the duct distal end portion 15 of the air intake noise reduction duct 11 are only connected by the three partition walls 21, 22, 23, production and assembly costs can be maintained low. In addition, since the upper wall 17 and the lower wall 18 each having the largest surface area of the flat duct distal end portion 15 are connected by the partition walls 21, 22, 23, not only can the rigidity of the air intake noise reduction duct 11 be enhanced with the partition walls 21, 22, 23 functioning as a reinforcement rib, but also generation of membrane surface vibrations of the upper wall 17 and the lower wall 18 which are flat and have the largest surface area can be restrained, generation of noise originating therein being thereby prevented.

Furthermore, since the duct distal end portion 15 of the air intake noise reduction duct 11 is formed flat, the layout of the relevant portion or the apparatus in a narrow space within an engine compartment can be facilitated. In particular, since the four air intake passages 24, 25, 26, 27 are formed into concentric arc-like configurations, the passage lengths of the respective air intake passages 24, 25, 26, 27 can be differentiated, while the air intake noise reduction duct 11 is made as compact as possible. In addition, the partition walls 21, 22, 23 are disposed in such a manner as to conform to the curved configuration of the duct distal end portion 15 of the air intake noise reduction duct 11, not only can increase in intake air resistance be suppressed by straightening air flows through the curved air intake passages 24, 25, 26, 27 with the partition walls 21, 22, 23, but also the air intake noise reduction duct can be made compact in size by constructing such that the length of the partition walls 21, 22, 23 becomes shorter as they are provided more radially inwardly.

Figure 5:
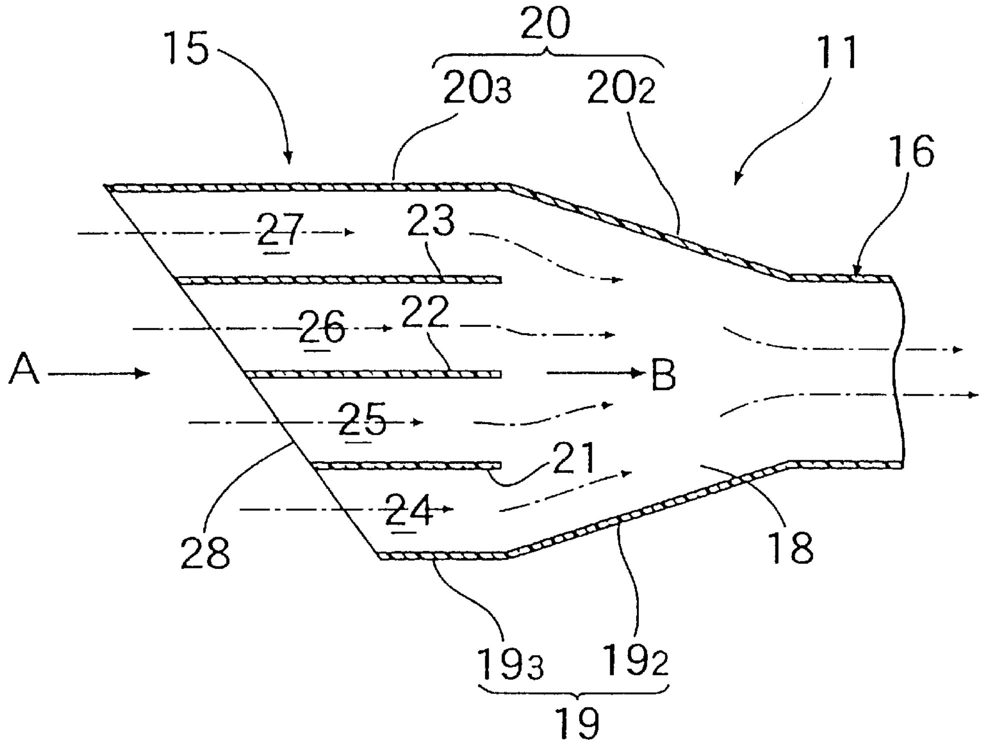
FIG. 5 is a sectional view showing a second embodiment of the present invention and corresponding to FIG. 3.

In an air intake noise reduction duct 11 according to a second embodiment of the present invention shown in FIG. 5, a duct distal end portion 15 is formed not curvedly but linearly. In other words, side walls 19, 20 of the duct distal end portion 15 each comprise a parallel portion $\mathbf{19}_3$, $\mathbf{20}_3$ on an upstream side and a tapered portion $\mathbf{19}_2$, $\mathbf{20}_2$ on a downstream side, and three partition walls 21, 22, 23 and four air intake passages 24, 25, 26 27 are formed linearly to be in parallel with one another. Therefore, a direction A in which air flows into opening ends 28 of the air intake passages 24, 25, 26, 27 comes to coincide with a direction B in which air flows out from the air intake passages 24, 25, 26, 27. In addition, the opening ends 28 are cut diagonally in order to differentiate the passage lengths of the four air intake passages 24, 25, 26, 27.

Since the partition walls 21, 22, 23 extend to identical positions on a downstream side, the volume of a portion of the flat distal end portion 15 where there exist no downstream portions of the partition walls 21, 22, 23 is reduced, and this is advantageous in enhancement of the rigidity of the flat distal end portion 15. Furthermore, since the diagonally cut opening ends 28 can be disposed so as to meet configurations of a mating member 100 as other members (such as an auxiliary machine or a vehicle body), the air intake noise reduction duct 11 can be disposed compactly within the engine compartment.

Figure 6:
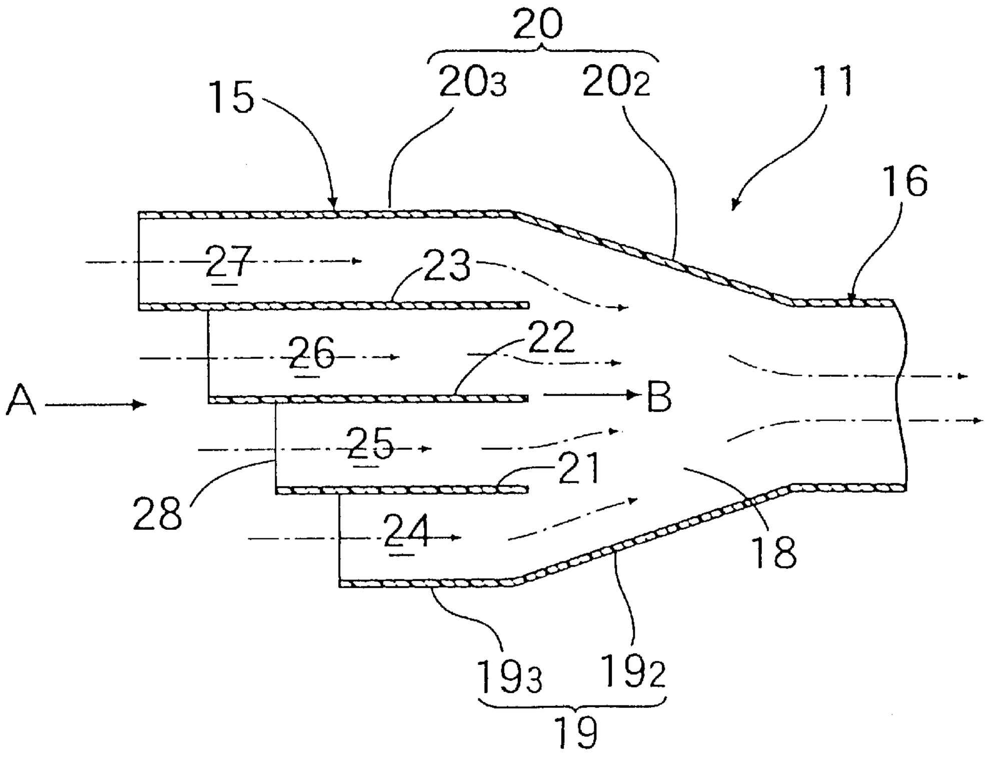
FIG. 6 is a sectional view showing a third embodiment of the present invention and corresponding to FIG. 3.

In an air intake noise reduction duct 11 according to a third embodiment of the present invention shown in FIG. 6, opening ends 28 are cut in a stepped fashion so that the passage lengths of four air intake passages 24, 25, 26, 27 are differentiated, and the remaining constructions thereof are identical to those of the second embodiment shown in FIG. 5.

Consequently, with the second and third embodiments, it is possible to obtain the same operational effect as that obtained with the first embodiment. However, since the air intake passages 24, 25, 26, 27 of the second and third embodiments are formed linearly, they are disadvantageous in compactibility over the fist embodiment, while they are advantageous in reduction in intake air resistance over the first embodiment.

Figure 7:
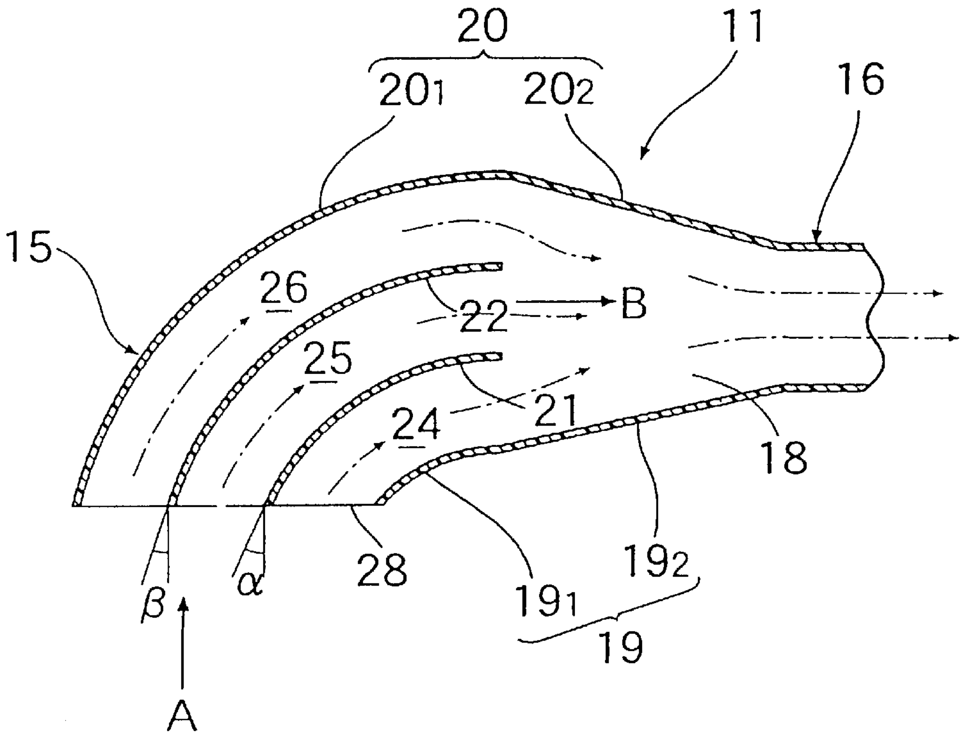
FIG. 7 is a sectional view showing a fourth embodiment of the present invention and corresponding to FIG. 3.
Figure 8:
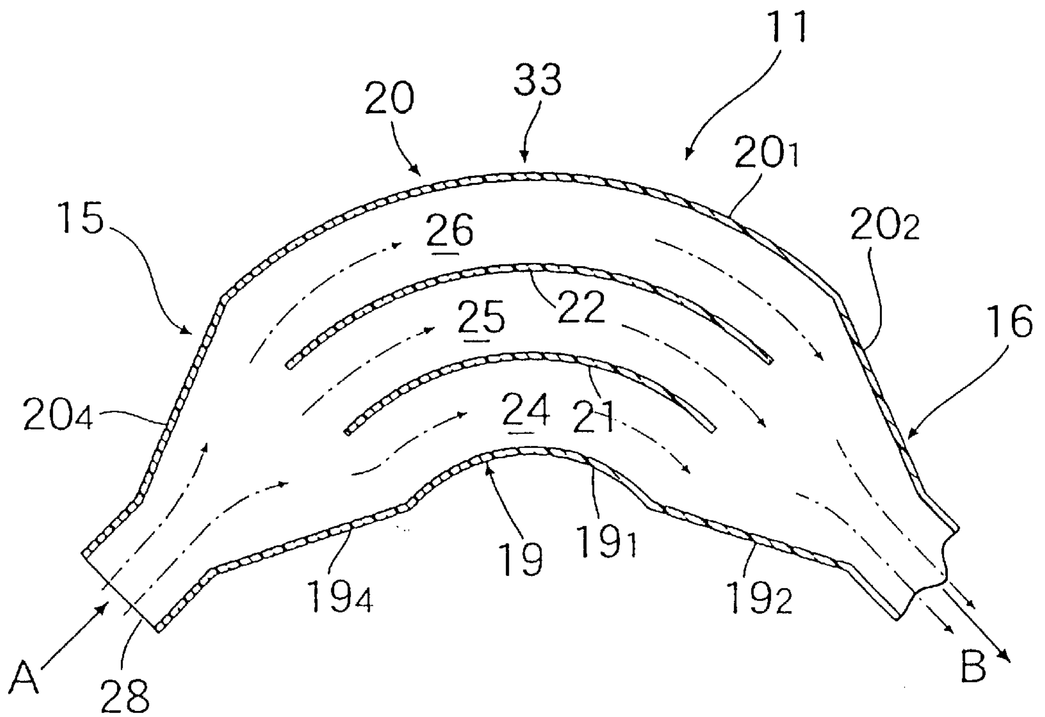
FIG. 8 is a sectional view showing a fifth embodiment of the present invention and corresponding to FIG. 3.

An air intake noise reduction duct 11 according to a fourth embodiment of the present invention shown in FIG. 7 is provided with a function to check intrusion of waterdrops from opening ends 28. In other words, as is clear when compared with the first embodiment shown in FIG. 3, tips of the partition walls 21, 22 of the fourth embodiment are inclined angles of $\alpha$ and $\beta$, respectively, relative to a direction A in which air flows in, and with this construction, waterdrops taken into the air intake noise reduction duct 11 together with air come to collide with the inclined tips of the partition walls 21, 22 so that they are prevented from intruding further into the air intake noise reduction duct 11.

In the air intake noise reduction duct according to the fourth embodiment, three air intake passages 24, 25, 26 are formed with two partition walls and it is different from the air intake noise reduction duct according to the first embodiment in that with the latter, there are formed four air intake passages 24, 25 26, 27 with three partition walls 21, 22, 23. However, the difference is not such that there is caused no particular difference in operational effect between the former and latter noise reduction ducts, and therefore the operational effect provided by the air intake noise reduction duct of the first embodiment can also be obtained with that of the fourth embodiment.

In an air intake noise reduction duct 11 according to a fifth embodiment of the present invention shown in FIG. 5 as being curved into an arc-like configuration, three air intake passages 24, 25, 26 which each have different lengths are formed with two partition walls which each have different lengths in an intermediate portion 33 provided between a duct distal end portion 15 and a duct proximal end portion 16. Side walls 19, 20 corresponding to the duct distal end portion 15 are formed into tapered portions $\mathbf{19}_4$, $\mathbf{20}_4$, and the cross-sectional area of the air intake noise reduction duct smoothly changes from an opening end 28 which is drawn to provide a circular cross-section to the flat intermediate portion. According to this embodiment, not only can the same operational effect as that of the first embodiment be obtained but also the intermediate portion 33 having a larger capacity can be shifted in accordance with space available within the engine compartment, the degree of freedom in layout being thereby enhanced.

Figure 9:
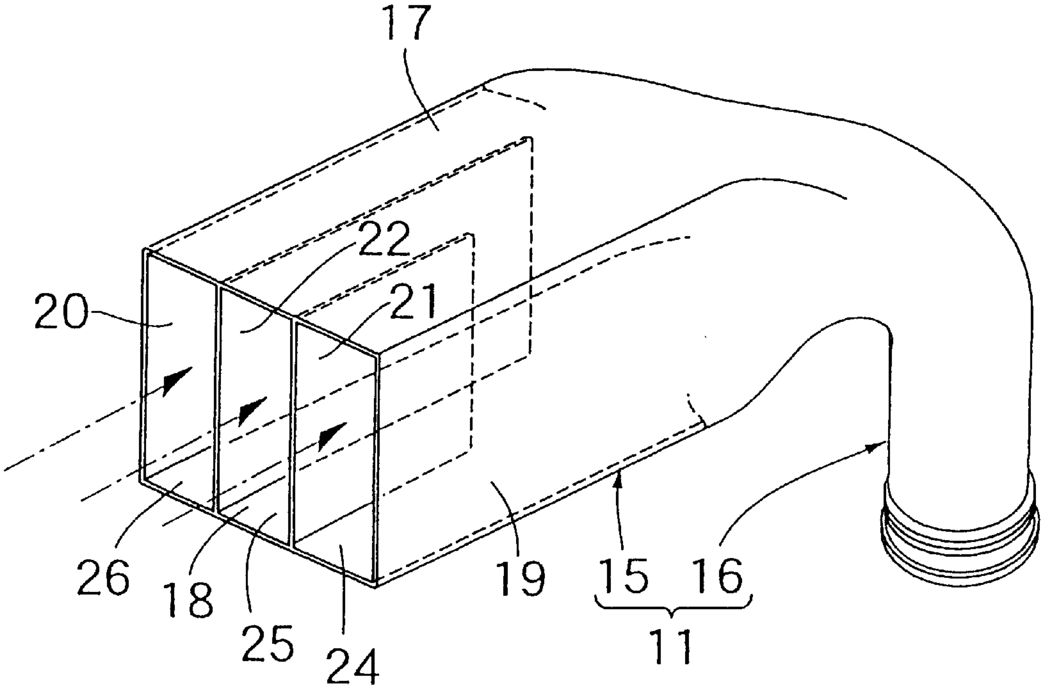
FIG. 9 is a perspective view showing a sixth embodiment of the present invention and corresponding to FIG. 3.
Figure 10A:
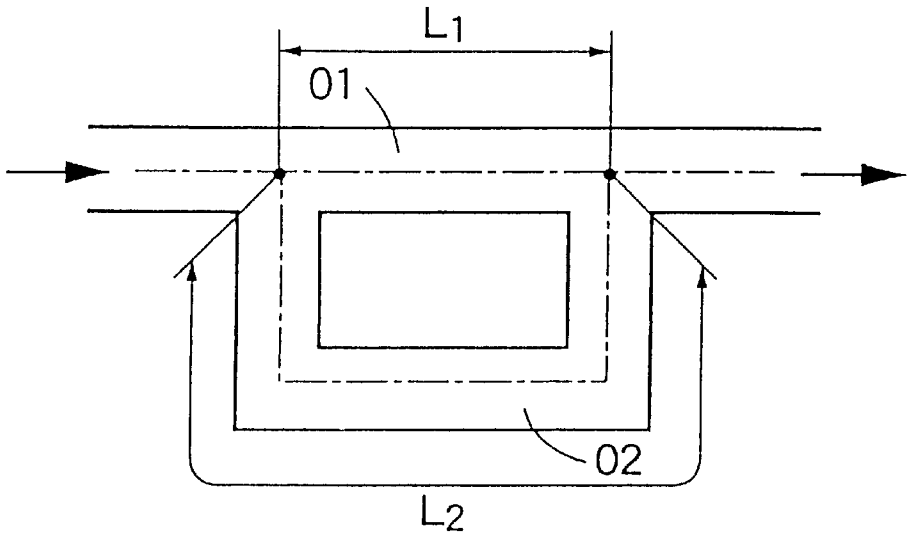
FIGS. 10A and 10B shows a conventional air intake noise reduction apparatus.
Figure 10B:
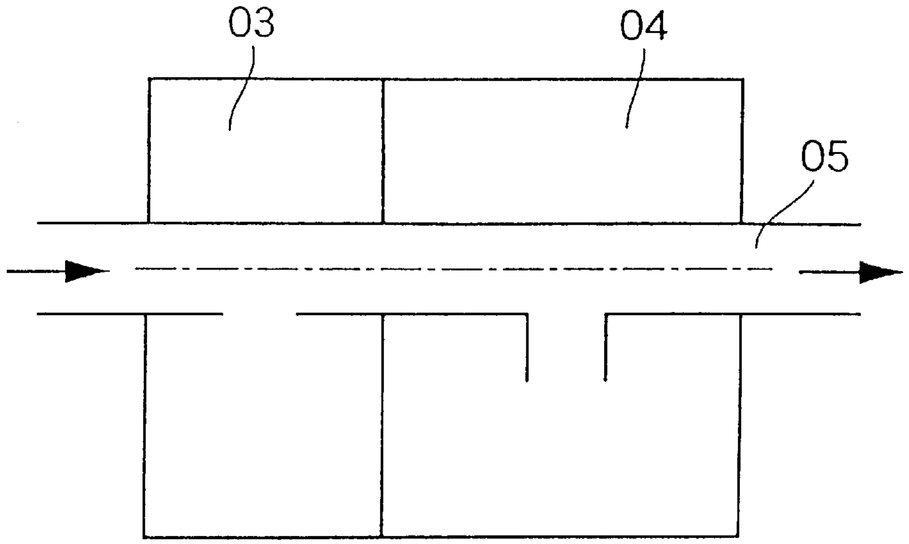

An air intake noise reduction duct 11 according to a sixth embodiment of the present invention shown in FIG. 9 is a modification from the second embodiment shown in FIG. 5 or the third embodiment shown in FIG. 6, and a duct distal end portion 15 thereof is not formed flat but formed so as to provide a square cross-section. An opening end 28 of the duct distal end portion 15 is cut normal to a direction in which air flows in, and the lengths of three air intake passages 24, 25, 26 are differentiated by terminating downstream ends thereof in a stepped fashion, while upstream ends thereof are in alignment with one another.

The sixth embodiment can also provide a similar operational effect to that of the first embodiment. With the air intake noise reduction duct according to the sixth embodiment, an upper wall 17 and a lower wall 18 originally have a small surface area and therefore it is hard for membrane surface vibrations to be generated. Due to this, the upper wall 17 and the lower wall 18 do not contribute to prevention of the generation of membrane surface vibrations as much as the other embodiments in which the upper walls 17 and the lower walls 18 each have the largest surface area of the duct distal end portions 15. In addition, the duct distal end portion 15 is not formed flat but formed so as to provide a square cross-section, the degree of freedom in layout can be enhanced depending on the configuration of space available within the engine compartment.

While the embodiments of the present invention have been described in detail, it should be appreciated that the present invention may be modified in design without departing from the scope and spirit thereof.

For instance, the number of air intake passages is not limited to four or three as described in the above embodiments, and any number of air intake passages equal to or larger than two may be selected. In addition, the air intake noise reduction duct may be flattened in a lateral direction according to the configuration of space available within the engine compartment, instead of being flattened in the vertical direction.

As has been described heretofore, according to the invention set forth in the present invention, air intake noise can be reduced effectively by forming a plurality of air intake passages which each have different passage lengths only with a compact and low-cost construction in which the partition walls are provided in the air intake noise reduction duct, and moreover, the rigidity of the air intake noise reduction duct can be enhanced with the partition walls functioning as a reinforcement rib.

In addition, in the first aspect of the present invention, since the partition walls are preferably formed such that they extend along a direction in which air is taken in, increase in intake air resistance can be suppressed to a minimum level.

According to the invention set forth in the second aspect of the present invention, air intake noise can be reduced effectively by forming a plurality of air intake passages which each have different passage lengths only with a compact and low-cost construction in which the partition walls are provided in the air intake noise reduction duct, and moreover since the partition walls connecting the opposed walls each having the largest surface area of the flat portion function as a reinforcement rib, the rigidity of the air intake noise reduction duct can be enhanced so as to effectively prevent membrane vibrations. Moreover, since the air intake noise reduction duct has the flat portion, the air intake noise reduction apparatus can be disposed even in a narrow space within the engine compartment.

Furthermore, according to the invention set forth in the third aspect of the present invention, air intake noise can be reduced effectively by forming a plurality of air intake passages which each have different passage lengths only with a compact and low-cost construction in which the partition walls are provided in the air intake noise reduction duct, and moreover, the rigidity of the air intake noise reduction duct can be enhanced with the partition walls functioning as a reinforcement rib. In addition, the curved portion of the air intake noise reduction duct is partitioned with the partition walls which extend along a curved configuration of the curved portion, not only can the air intake noise reduction duct be made more compact in size, but also increase in intake air resistance can be suppressed by straightening air flows at the curved portion.

Moreover, according to the invention set forth in the fourth aspect of the present invention, since at least three air intake passages are formed with at least two partition walls, the air intake noise reduction effect can be enhanced. In addition, since the partition wall situated inwardly of the curved portion in the curved direction is made shorter in length, the air intake noise reduction duct can be made more compact in size.

Futhermore, according to the invention set forth in the fifth aspect of the present invention, air intake noise can be reduced effectively by forming a plurality of air intake passages which each have different passage lengths only with a compact and low-cost construction in which the partition walls are provided in the air intake noise reduction duct, and moreover, the rigidity of the air intake noise reduction duct can be enhanced with the partition walls functioning as a reinforcement rib. In addition, since the direction of air intake and the direction of the partition walls are caused to intersect with each other at the entry portion of the air intake noise reduction duct, intrusion of water or the like into the interior of the air intake noise reduction duct can be checked.

While there has been described in connection with the preferred embodiment of the invention, it will be obvious to those skilled in the art that various changes and modifications may be made therein without departing from the invention, and it is aimed, therefore, to cover in the appended claim all such changes and modifications as fall within the true spirit and scope of the invention.

What is claimed is:

1. An air intake noise reduction duct for an automotive vehicle for reducing air intake noise with an air intake noise reduction duct (11) for inducting air into an engine of said automotive vehicle, wherein a plurality of air intake passages (24, 25, 26, 27) which each have different passage lengths are formed by partitioning said air intake noise reduction duct (11) with partitioned walls (21, 22, 23), wherein the plurality of air intake passages (24, 25, 26, 27) direct air into the engine and have identical cross sectional areas and said partition walls (21, 22, 23) extend to identical positions on a downstream side of the air intake noise reduction duct (11).

2. The air intake noise reduction duct according to claim 1, wherein said air intake noise reduction duct (11) is partitioned by said partition walls (21, 22, 23) which extend along an intake air flow direction.

3. The air noise reduction duct according to claim 1, wherein said plurality of air intake passages (24, 25, 26, 27) which each have different passage lengths are formed by connecting opposed walls (17, 18) each having a largest surface area of a flat portion provided in said air intake noise reduction duct (11) with said partitioned walls (21, 22, 23) extending along an intake air flow direction.

4. The air intake noise reduction duct according to claim 1, wherein said plurality of air intake passages (24, 25, 26, 27) which each have different passage lengths are formed by partitioning a curved portion provided in said air intake noise reduction duct (11) with said partition walls (21, 22, 23) extending so as to conform to a curved configuration of said curved portion.

5. The air intake noise reduction duct according to claim 4, wherein the length of said partition walls (21, 22, 23) is made shorter as said partitioned walls are situated more inwardly of said curved portion in a curved direction.

6. The air intake noise reduction duct according to claim 4, wherein said plurality of air intake passages (24, 25, 26, 27) are formed by connecting opposed walls (17, 18) each having a largest surface area of a flat portion provided in said air intake noise reduction duct (11) with said partition walls (21, 22, 23) extending along an intake air flow direction.

7. The air intake noise reduction duct according to claim 1, wherein the intake air flow direction and the direction of said partition walls (21, 22, 23) are made to intersect with each other at an entry portion of said air intake noise reduction duct (11).

8. The air intake noise reduction duct according to claim 7, wherein said plurality of air intake passages (24, 25, 26, 27) are formed by connecting opposed walls (17,18) each having a largest surface area of a flat portion provided in said air intake noise reduction duct (11) with said partition walls (21, 22, 23).

9. The air intake noise reduction duct according to claim 1, wherein an opening end (28) of said air intake noise reduction duct (11) is shaped so as to meet configurations of a mating member (100).

10. The air intake noise reduction duct according to claim 9, wherein said mating member is one of a vehicle body and an auxiliary machine.

11. The air intake noise reduction duct according to claim 9, wherein said plurality fair intake passages (24, 25, 26, 27) are formed by connecting opposed walls (17, 18) each having a largest surface area of a flat portion provided in said air intake noise reduction duct (11) with said partition walls (21, 22, 23) extending along an intake air flow direction.

12. The air intake noise reduction duct according to claim 1, wherein said plurality of air intake passages (24, 25, 26, 27) which each have different passage lengths are formed by connecting opposed walls (17, 18) each having a largest surface area of a flat portion provided in said air intake noise reduction duct (11) with said partition walls (21, 22, 23).

13. An air intake noise reduction duct for reducing intake noise of air inducted into an engine of an automotive vehicle, wherein a plurality of intake passages (24, 25, 26, 27) which each having different passage lengths are formed by partitioning said air intake noise reduction duct (11) with partition walls (21, 22, 23), and by connecting flat opposed walls (17, 18) each having a largest surface area of flat portions provided in said air intake noise reduction duct (11) with said partition walls (21, 22, 23), characterized in that the air intake noise reduction duct is made of a single member of synthetic resin, and that the plurality of intake passages (24, 25, 26, 27) separately open directly to the outside of the air intake noise reduction duct (11), wherein the plurality of air intake passages (24, 25, 26, 27) direct air into the engine and have identical cross sectional areas and said partition walls (21, 22, 23) extend to identical positions on a downstream side of the air intake noise reduction duct (11).

* * * * *